United States Patent
Kuo et al.

(10) Patent No.: US 10,973,863 B2
(45) Date of Patent: *Apr. 13, 2021

(54) METHOD FOR REGULATING, PREVENTING AND/OR TREATING PULMONARY INJURY

(71) Applicant: SINPHAR PHARMACEUTICAL CO., LTD., Dongshan Township, Yilan County (TW)

(72) Inventors: Han-Peng Kuo, Dongshan Township, Yilan County (TW); Ai-Ling Yeh, Dongshan Township, Yilan County (TW); Chao-Jih Wang, Zhejiang (CN)

(73) Assignee: SINPHAR PHARMACEUTICAL CO., LTD., Dongshan Township, Yilan County (TW)

( * ) Notice: Subject to any disclaimer, the term of this patent is extended or adjusted under 35 U.S.C. 154(b) by 0 days.

This patent is subject to a terminal disclaimer.

(21) Appl. No.: 15/860,717

(22) Filed: Jan. 3, 2018

(65) Prior Publication Data

US 2018/0214498 A1    Aug. 2, 2018

Related U.S. Application Data

(60) Provisional application No. 62/441,747, filed on Jan. 3, 2017.

(51) Int. Cl.
*A61K 36/076*    (2006.01)
*A61P 11/14*    (2006.01)

(52) U.S. Cl.
CPC ............ *A61K 36/076* (2013.01); *A61P 11/14* (2018.01)

(58) Field of Classification Search
None
See application file for complete search history.

(56) References Cited

U.S. PATENT DOCUMENTS

| | | | | |
|---|---|---|---|---|
| 9,370,540 B2 * | 6/2016 | Lin | .......................... | C07J 9/005 |
| 2002/0031559 A1 * | 3/2002 | Liang | ....................... | A61K 9/02 |
| | | | | 424/725 |
| 2011/0189220 A1 * | 8/2011 | Yang | .................... | A61K 36/068 |
| | | | | 424/195.15 |
| 2015/0335690 A1 * | 11/2015 | Lin | .......................... | C07J 9/005 |
| | | | | 424/195.15 |

FOREIGN PATENT DOCUMENTS

| | | |
|---|---|---|
| CN | 1611235 | 5/2005 |
| CN | 104547361 | 4/2015 |
| CN | 104688782 | 6/2015 |
| CN | 104958305 | 10/2015 |
| CN | 105085598 | 11/2015 |
| TW | 201544114 | 12/2015 |

OTHER PUBLICATIONS

Rios 2011 (Chemical Constituents and Pharmacological Properties of Poria cocos; Planta Med 77:681-691). (Year: 2011).*
Churg et al. 2012 (Matrix Metalloproteinases in Lung Health and Disease; European Respiratory Journal 39(1): 197-209). (Year: 2012).*
Arikan et al. 2015 (The relationship between cough-specific quality of life and abdominal muscle endurance, fatigue, and depression in patients with COPD; International Journal of COPD 10: 1829-1835) (Year: 2015).*
Langlands 1967 (The dynamics of cough in health and in chronic bronchitis, Thorax 22:88) (Year: 1967).*
Houghton 2013 (Mechanistic links between COPD and lung cancer; Nature Reviews Cancer 13: 233-245) (Year: 2013).*
Thomas et al. 2000 (Differential expression of matrix metalloproteinases and their inhibitor in non-small cell lung cancer; Journal of Pathology, 190: 150-156) (Year: 2000).*
O'Shea et al. 2012 (Lung Herniation after Cough-Induced Rupture of Intercostal Muscle; New England Journal of Medicine). (Year: 2012).*
International Search Report and Written Opinion of International Application No. PCTCN2018/070104 dated Mar. 27, 2018.
Ma, L. et al., "Research progress of Poria cocos", Asia-Pacific Traditional Medicine, 2015, vol. 11, No. 12, pp. 55-59.
Lee, S. R. et al., "Bioactivity-guided isolation of anti-inflammatory triterpenoids from the sclerotia of Poria cocos using LPS-stimulated Raw264.7 cells," Bioorganic Chemistry, vol. 70, Feb. 2017, pp. 94-99.
Kuo, C. H. et al., "Mechanism and treatment of airway remodeling", Journal of Internal Medicine of Taiwan, 2009, vol. 20(2), pp. 129-138.
Expression of Ets-1 and MMP9 in lung cancer and their relationship with invasion and metastasis, 2015.
Gao, T. et al., "Advances in research of lung injury biomarkers", Chinese Journal of New Drugs, 2013, vol. 22(4), pp. 429-432.
Cheng, X. et al. "Triterpenes from Poria Cocos suppress growth and invasiveness of pancreatic cancer cells through the downregulation of MMP-7." International Journal of Oncology. 42: 1869-1874, 2013.
Gongxun, X. et al. "Combination therapy of Chinese and Western medicines for the acute exacerbation of chronic obstructive pulmonary disease (Forty-five cases)." TCM Res. Jul. 2012 vol. 25 No. 7.

* cited by examiner

*Primary Examiner* — Mary Maille Lyons
(74) *Attorney, Agent, or Firm* — Ping Wang; Morris, Manning & Martin LLP (57) ABSTRACT

A method for regulating, preventing, and/or treating pulmonary injury, and/or for regulating, preventing, and/or treating pulmonary injury-related diseases is provided. The method comprises administering to a subject in need an effective amount of FU-LING extract, tumulosic acid, dehydrotumulosic acid, dehydrotrametenolic acid, and/or poricoic acid A.

16 Claims, 6 Drawing Sheets

METHOD FOR REGULATING, PREVENTING AND/OR TREATING PULMONARY INJURY

FIELD OF THE INVENTION

The present invention relates to the uses of a FU-LING (*Poria cocos*) extract and/or its active ingredients, particularly to the uses in regulating, preventing and/or treating pulmonary injury, and/or in regulating, preventing and/or treating pulmonary injury-related diseases, in particular, the aforementioned pulmonary injury is induced by particulate matter (PM).

BACKGROUND OF THE INVENTION

Lung, the central part of respiratory system, consists of bronchi, bronchioles, alveolar ducts and alveoli and has a spongiform structure that is soft and flexible. The primary function of lung in human body is to exchange gas, including the transportation of oxygen from the air to the blood and the release of carbon dioxide from the blood to the outside of body. Recent studies indicated that the decrement or loss of pulmonary functions induced by pulmonary injury would not only affect the entire respiratory system but also affect the whole body's water metabolism, blood circulation and immune system. Therefore, even if the pulmonary injury is mild, it cannot be ignored.

The causes of pulmonary injuries include serious chest trauma, inhalation of harmful substances (e.g., toxic gas, gastric content, seawater, etc.), pulmonary infections, etc. Along with the economic and industrial development, the long-term emission of gas wastes (including particulate matter, sulfur dioxide, carbon monoxide, nitrogen dioxide, ozone, etc.) from vehicles, factories and incineration has already caused serious air pollution. Traffic pollution, industrial pollution, agricultural pollution and daily life pollution (e.g., cooking oil fumes, smoking, etc.) are major sources of particulate pollutants suspended in the air, which are generally called as particulate matter and are complicated in composition and various in form. Particulate matter is an indicative pollutant for evaluating the air pollution and quantizing the health hazards, and can be generally divided into coarse particulate matter, fine particulate matter and ultrafine particulate matter depending on the particle size. Among the particulate matter, PM10 and PM2.5 refer to the suspended particles having an aerodynamic particle diameter of no more than 10 μm and no more than 2.5 μm, respectively. Particulate matter can get into respiratory ducts through respiration, and sediment at different locations of the respiratory ducts depending on its size. In general, particulate matter with a particle size of more than 10 μm will be blocked by nasal hairs and expelled from the body by coughing. However, particulate matter with a particle size of no more than 10 μm (such as PM10 and PM2.5) may enter the lung and thus deposit in the alveolar tissue.

The chemical composition of PM2.5 include the following two groups: original particulate matter and derivative particulate matter, wherein the former primarily includes heavy metals, dioxins, polyaromatics and organic carbon, and the latter primarily includes nitrates and sulfates (sulfites). Since PM2.5 is small in volume and light in weight, it can stay in the atmosphere for a long time and spread out everywhere, thereby causing a wide range of air pollution.

Researchers have found that when PM2.5 enters the lung and deposits in the alveolar tissue of a subject, it may cause pulmonary injury and pulmonary inflammation, and lead to the symptoms such as sensing suppression in the chest (decrement in lung capacity and increment in respiratory resistance), coughing, increment in sputum production, etc., thereby affecting the health condition and life quality of the subject. The serious pulmonary injury induced by PM2.5 or other factors may cause a decrement in or loss of pulmonary functions, which may even become chronic obstructive pulmonary disease (COPD), idiopathic pulmonary fibrosis (IPF), emphysema, chronic bronchitis (CB), acute respiratory distress syndrome (ARDS), bronchopulmonary dysplasia (BPD), bronchiolitis obliterans (BO), and/or cryptogenic organizing pneumonia (COP). However, there is no effective approach for isolating PM2.5, and thus, people are still prone to the air pollution such as the gas wastes from cars, motorcycles, factories and thermal power plant, daily oil fumes, smoking, etc. Therefore, there is necessity and urgency for continuously developing a drug or a method for regulating, preventing and/or treating pulmonary injury, and/or for regulating, preventing, and/or treating pulmonary injury-related diseases, to alleviate or release the symptoms of sensing suppression in the chest (increasing lung capacity and reducing respiratory resistance), reduce coughing, and/or reduce sputum production, thereby alleviating the impact of air pollution on the health condition and life quality of a subject.

Inventors of the present invention found that FU-LING extract and its ingredients such as tumulosic acid (TA), dehydrotumulosic acid (DTA), dehydrotrametenolic acid (DTTA) and poricoic acid A (PAA) are all effective in inhibiting the secretion, expression and activity of matrix metalloproteinases (MMPs), inhibiting the secretion and accumulation of collagen and inhibiting the expression of mucin, and thus can be used for regulating, preventing, and/or treating pulmonary injury (especially pulmonary injury caused by particulate matter), and thus, the aforementioned extract and ingredients can be used for providing a composition for regulating, preventing and/or treating pulmonary injury, and/or for regulating, preventing and/or treating pulmonary injury-related diseases.

SUMMARY OF THE INVENTION

An objective of the present invention is to provide a use of a FU-LING extract in the manufacture of a composition, wherein the composition is used for regulating, preventing and/or treating pulmonary injury, and/or for regulating, preventing and/or treating pulmonary injury-related diseases. Preferably, the FU-LING extract comprises at least one of tumulosic acid, dehydrotumulosic acid, dehydrotrametenolic acid and poricoic acid A. Preferably, the FU-LING extract is a polar solvent extract of FU-LING, and the polar solvent is selected from a group consisting of water, C1-C4 alcohols, and combinations thereof. Preferably, the FU-LING extract is an extract of at least one of FU-LING meat, FU-LING epidermis, and FU-LING fermentation product. The composition is a food composition or a pharmaceutical composition, wherein the food composition is a health food, a dietary supplement, a functional food, a nutritional supplement food or a special nutritional food.

Another objective of the present invention is to provide a use of an active ingredient in the manufacture of a composition, wherein the composition is used for regulating, preventing and/or treating pulmonary injury, and/or is used for regulating, preventing and/or treating pulmonary injury-related diseases, and the active ingredient is selected from a group consisting of tumulosic acid, dehydrotumulosic acid, dehydrotrametenolic acid, poricoic acid A, and combinations thereof. Preferably, the active ingredient is administered as a plant extract or a fungal extract. The composition is a food composition or a pharmaceutical composition, wherein the food composition is a health food, a dietary supplement, a functional food, a nutritional supplement food or a special nutritional food.

Still another objective of the present invention is to provide a composition which is used for regulating, preventing and/or treating pulmonary injury, and/or is used for regulating, preventing and/or treating pulmonary injury-related diseases, wherein the composition is a food composition or a pharmaceutical composition and comprises an effective amount of the aforementioned active ingredients or FU-LING extracts. The food composition is a health food, a dietary supplement, a functional food, a nutritional supplement food or a special nutritional food.

Yet another objective of the present invention is to provide a method for regulating, preventing and/or treating pulmonary injury, and/or for regulating, preventing and/or treating pulmonary injury-related diseases, comprising administering to a subject in need an effective amount of the aforementioned active ingredients or FU-LING extract. Preferably, the aforementioned active ingredient or FU-LING extract is administered to the subject as a food composition or a pharmaceutical composition, and the food composition is a health food, a dietary supplement, a functional food, a nutritional supplement food or a special nutritional food.

The above compositions or methods in accordance with the present invention are effective in inhibiting the expression and/or the activity of Matrix metalloproteases (MMPs) and/or mucins, and thus can be used for regulating, preventing and/or treating pulmonary injury or the following pulmonary injury-related diseases: chronic obstructive pulmonary disease, idiopathic pulmonary fibrosis, emphysema, chronic bronchitis, acute respiratory distress syndrome, bronchopulmonary dysplasia, bronchiolitis obliterans, and cryptogenic organizing pneumonia. Particularly, the aforementioned pulmonary injury is that caused by particulate matter. The MMPs include such as matrix metalloproteinase-9 (MMP-9) and matrix metalloproteinase-12 (MMP-12). The mucins include such as Mucin 5AC.

The detailed technology and some of embodiments implemented for the present invention will be described in the following paragraphs for persons skilled in the art to well appreciate the features of the claimed invention.

BRIEF DESCRIPTION OF THE DRAWINGS

FIGS. 1A to 1C are the results of Western blot, showing the effects of FU-LING extract on the lipopolysaccharides (LPS)-induced increment in MMPs expression, wherein

FIGS. 2A to 2C are the results of Western blot, showing the effects of tumulosic acid on the LPS-induced increment in MMPs expression, wherein

FIGS. 3A to 3C are the results of Western blot, showing the effects of poricoic acid A on the LPS-induced increment in MMPs expression, wherein FIGS. 4A and 4B are the results of Western blot, showing the effects of tumulosic acid and poricoic acid A on the LPS-induced increment in Mucin 5AC expression, wherein

DESCRIPTION OF THE PREFERRED EMBODIMENTS

The following will describe some of the embodiments of the present invention in detail. However, without departing from the spirit of the present invention, the present invention may be embodied in various embodiments and should not be limited to the embodiments described in the specification, in addition, unless otherwise indicated herein, the expression "a," "an," "the," or the like recited in this specification (especially in the claims) are intended to include both the singular or plural forms. The term "an effective amount" recited in this specification refers to the amount of the substance that can at least partially alleviate pulmonary injury and/or pulmonary injury-related diseases in a suspected subject when administered to the subject. The term "subject" recited in this specification refers to a mammalian, including human and non-human animals.

The term "pulmonary injury" recited in this specification refers to the destruction or loss to the function or structural integrity of lung. The term "active expression" of MMPs recited in this specification refers to the sum of secretion level, expression level and activity of MMPs. The term "regulate pulmonary injury" or "regulating pulmonary injury" recited in this specification refers to alleviating or releasing the symptoms of sensing suppression in the chest (i.e., to increase lung capacity and/or reduce respiratory resistance), reducing coughing, and/or reducing sputum production. The term "treat" or "treating" recited in this specification should not be construed as treating a subject until the subject is completely recovered, and includes maintaining the progression or symptoms of the diseases in a substantially static state, increasing the recovery rate of a subject, alleviating the severity of a particular condition of illness, or enhancing the quality of life of a patient.

The numerical ranges (e.g., 5 to 100) recited in this specification should be construed as including all of the rational numbers in the ranges and the ranges consisting of any rational numbers in the ranges. Therefore, the numerical ranges recited in this specification should include all the possible combinations of numerical values between the lowest value and the highest value listed therein. In addition, the word "about" as used herein substantially represents values within ±10% of the stated value and more preferably within ±5%.

Herbal FU-LING refers to the dried sclerotium of *Poria cocos* (Schw.) Wolf. *Poria cocos* (Schw.) Wolf often parasitizes the roots of pine trees. The external layer of *Poria cocos* (Schw.) Wolf is a light or dark brown color (known as *Poria cocos* epidermis) and the inside of *Poria cocos* (Schw.) Wolf is a pink or white color (known as *Poria cocos* meat). The FU-LING fermentation products refer to the products obtained by inoculating the *Poria cocos* (Schw.) Wolf onto a substrate, and then placing the inoculated substrate under an environment with a temperature ranging from 20° C. to 35° C. and a relative humidity ranging from 30% to 70% to conduct a dark fermentation for several weeks to several months.

As indicated above, the particulate matter (e.g., PM2.5) that enters the lung and deposits in the alveolar tissue may stimulate the pulmonary tissue and cause an abnormal or a hyperactive immune response, and thus may lead to pulmonary injury and symptoms such as the decrement in lung capacity, increment in respiratory resistance, coughing, and increment in sputum production. Researchers have found that when the animal's pulmonary tissue is stimulated, the active inflammatory cells will secrete MMPs that would destroy the pulmonary tissue structure, cause more serious pulmonary injury, and lead to decrement in or loss of pulmonary functions, and even cause the diseases such as chronic obstructive pulmonary disease, idiopathic pulmonary fibrosis, emphysema, chronic bronchitis, and acute respiratory distress syndrome. Moreover, diseases such as bronchopulmonary dysplasia, bronchiolitis obliterans, and cryptogenic organizing pneumonia are also associated with the hyperactivation of MMPs. For example, the hyperactive expression of MMPs in the inflammatory cells will damage the pulmonary tissue.

When there is stimulation or damage to the pulmonary tissue, the response mechanism in animals would instantaneously activate to promote the secretion of collagen in lung fibroblasts. However, the hypersecretion of collagen may also cause fibrosis of pulmonary tissues, including lung parenchyma (e.g., pulmonary alveolus) and lung interstitium (e.g., connective tissue and blood vessels). In other words, in the absence of any therapies, the continuous stimulation or damage to the pulmonary tissue may result in lung fibrosis.

MMPs refers to a group of endopeptidases and have particular dependence of zinc ion as well as the ability to degrade extracellular matrix (ECM), and thus, MMPs can regulate angiogenesis and tissue reconstruction. According to the abilities of recognizing and degrading matrix proteins, MMPs can be generally classified into type I matrix metalloproteinases (e.g., collagenase), type II matrix metalloproteinases (e.g., gelatinase and elastase), type III matrix metalloproteinases (e.g., lysozyme) and type IV matrix metalloproteinases (e.g., membrane-type matrix metalloproteinase).

MMP-9, which is also known as gelatinase B, belongs to type II matrix metalloproteinases and is a gelatinase having the largest molecular weight in the MMPs family and is presented in various organisms. In animal bodies, MMP-9 is secreted as a proenzyme and is able to degrade gelatin, collagen IV and collagen V, and thus, MMP-9 is known as the primary enzyme on regulating the degradation of the extracellular matrix. MMP-12, which is an elastase, also belongs to type II matrix metalloproteinases and is able to degrade elastin, and thus, MMP-12 is also an important enzyme on regulating the degradation of extracellular matrix.

Under normal circumstances, the production and activity of MMP-9 and MMP-12 in animal tissues are regulated strictly, and thus MMP-9 and MMP-12 would not be activated easily. But in the presence of special stimuli (e.g., pulmonary tissue is stimulated by the smoking fume or the harmful particles in air), the epithelial cells, smooth myocytes, fibroblasts, and endothelial cells in the pulmonary tissue all can be induced to produce MMP-9, and the epithelial cells, smooth myocytes, macrophages and neutrophils in the pulmonary tissue all can be induced to produce MMP-9 and MMP-12. MMP-9 and MMP-12 thus produced can further destroy pulmonary tissue and subject the inflammatory cells (e.g., macrophages, neutrophils, mast cells, eosinophils, lymphocytes, neutral killer cells and dendritic cells) to move out and gather at the target organ, thereby aggravating the inflammation in the tissue. There are studies indicating that the disorder in the active expression (hypersecretion car hyperactivation) of MMP-9 and/or MMP-12 are closely associated with the occurrence of pulmonary injury.

If the pulmonary tissue is stimulated, the hypersecretion of airway mucus will also occur. Airway mucus hypersecretion is one of the specific histologic characteristics for pulmonary injury-related diseases such as chronic obstructive pulmonary disease and chronic bronchitis, and involves complicated mechanisms. Increased production of sputum Could be observed in the subject with airway mucus hypersecretion. The increased sputum will accumulate in the trachea and lung, thereby making the trachea narrow, increasing the respiratory resistance, and even causing a serious airway obstruction.

High molecular weight mucin is the most important component in the airway mucus, wherein the content of mucin 5AC is highest and that of mucin 4B is secondary. It has been noticed that the sputum of patients suffering from pulmonary injury-related diseases (such as chronic obstructive pulmonary disease and emphysema) exhibits an increased expression level of mucin 5AC and mucin 4B, and this reveals that the airway mucus hypersecretion is associated with the overexpression of the two mucins. Currently, the molecular mechanism of production and secretion of airway mucus can be well illustrated via an in vitro cellular experimental model (e.g., human lung mucoepidermoid cell line, NCI-H1292) or an animal experimental model.

Inventors of the present invention found that FU-LING extract and its ingredients such as tumulosic acid, dehydrotumulosic acid, dehydrotrametenolic acid and poricoic acid A are effective in inhibiting the LPS-induced increments in the active expression of MMPs and/or the LPS-induced increments in the expression of mucins, and/or inhibiting the TGF-β-induced hypersecretion and hyperaccumulation of collagen, and thus can be used for regulating, preventing and/or treating pulmonary injury, and/or can be used for regulating, preventing and/or treating pulmonary injury-related diseases, wherein the pulmonary injury particularly refers to that caused by particulate matter. The pulmonary injury-related diseases include chronic obstructive pulmonary disease, idiopathic pulmonary fibrosis, emphysema, chronic bronchitis, acute respiratory distress syndrome, bronchopulmonary dysplasia, bronchiolitis obliterans, and cryptogenic organizing pneumonia. It is believed that the FU-LING extract, tumulosic acid, dehydrotumulosic acid, dehydrotrametenolic acid and/or poricoic acid A adopted in accordance with the present invention can regulate, prevent and/or treat pulmonary injury, and/or can regulate, prevent and/or treat pulmonary injury-related diseases via decreasing the active expression of MMPs, especially MMP-9 and/or MMP-12, and/or via decreasing the expression of mucins, especially mucin 5AC. It is also believed that the extract, tumulosic acid, dehydrotumulosic acid, dehydrotrametenolic acid and/or poricoic acid A adopted in accordance with the present invention can increase lung capacity, decrease respiratory resistance, reduce coughing, and/or reduce sputum production by regulating, preventing and/or treating pulmonary injury, and/or by regulating, preventing and/or treating pulmonary injury-related diseases.

Therefore, the present invention provides the uses of a FU-LING extract in regulating, preventing, and treating pulmonary injury, and/or in regulating, preventing and/or treating pulmonary injury-related disease. Particularly, the pulmonary injury is caused by particulate matter. The uses include a use of the FU-LING extract in the manufacture of a composition used for regulating, preventing and/or treating pulmonary injury, and/or for regulating, preventing and/or treating pulmonary injury-related disease, a method comprising administering to a subject in need an effective amount of a FU-LING extract so as to regulate, prevent and/or treat pulmonary injury, and/or to regulate, prevent and/or treat a pulmonary injury-related disease, and providing a composition comprising the FU-LING extract.

The FU-LING extract adopted in accordance with the present invention can be a liquid extract provided by extracting FU-LING material with a polar solvent, wherein the FU-LING material can be a FU-LING meat, FU-LING epidermis, FU-LING fermentation product or combinations thereof, and the polar solvent can be water, C1-C4 alcohols or combinations thereof. Preferably, the polar solvent is water, ethanol or a combination thereof. The ratio of the polar solvent and FU-LING can be optionally adjusted, in general, there is no limitation of the amount of polar solvent as long as the material can be evenly dispersed in the polar solvent, in one embodiment of the present invention, the extraction was carried out with the use of ethanol as the polar solvent at a volume ratio of FU-LING material: ethanol=1:8.

In the aforementioned extraction procedures, the extraction is conducted for a period of time to achieve the desired degree of extraction. For example, when ethanol is used as the polar solvent, the extraction is usually conducted for at least 1 hour, preferably at least 2 hours, and more preferably at least 3 hours. In addition, the extraction can be optionally accompanied with other operations such as a removal of water-soluble impurities (i.e., adding a suitable amount of water into the liquid extract to remove the water-soluble impurities), decoction, cooling, filtering, vacuum concentration, and resin column chromatography.

The FU-LING extract adopted in accordance with the present invention can be also a dry matter provided by drying the aforementioned liquid extract. To achieve as high of an extraction efficacy as possible, the FU-LING material can be repeatedly extracted with the same or different polar solvents optionally and the extracts thus obtained are combined prior to conducting the drying procedure. Also, each extract operation can be carried out with the same or different polar solvent.

Optionally, the FU-LING liquid extract or the extract dry matter can be sequentially subjected to an alkalization and an acidification once or more times to increase the content of total triterpenoids (especially tumulosic acid and dehydrotumulosic acid) in the liquid extract or the dry matter, if the dry matter is subjected to the one or more times of alkalization and acidification in sequence, the product thus provided can be subjected to the drying procedure again to provide a final extract dry matter.

The term "alkalization" or "alkalize" recited in the specification refers to increasing the pH value of a material (in the present invention, refers to the aforementioned liquid extract obtained by extracting the FU-LING material with a polar solvent) by any suitable alkaline substance. In general, the pH value of material is increased to no less than about 10 by the alkalization; preferably to no less than about 11, and more preferably to no less than about 12. In one embodiment of the present invention, the 1N sodium hydroxide was added during the alkalization to increase the pH value of the extract to about 12. After increasing the pH value of the extract, the alkalization is carried out with a raising temperature. For example, the alkalization is carried out at a temperature of no less than 50° C., and preferably no less than 60° C. As shown in the appended examples, the alkalization could be carried out at a temperature such as 70° C.

The term "acidification" or "acidify" recited in the specification refers to decreasing the pH value of a material (in the present invention, refers to the aforementioned alkalized liquid extract). In one embodiment of the present invention, hydrochloric acid was used to decrease the pH value of the alkalized liquid extract. In general, there is no particular limitation to the level of the pH value decreased by the acidification, as long as the pH value is decreased. For example, the pH value of the alkalized liquid extract can be decreased for at least about 3.0, and preferably for at least about 4.0. In one embodiment of the present invention, the pH value of alkalized liquid extract was decreased to about 7 during the acidification.

As shown in appended examples, the FU-LING extract adopted in accordance with the present invention comprises at least one ingredient selected from a group consisting of tumulosic acid, dehydrotumulosic acid, dehydrotrametenolic acid, and poricoic acid A.

The present invention also provides a use of an active ingredient in regulating, preventing and/or treating pulmonary injury, and/or in regulating, preventing and/or treating pulmonary injury-related disease, wherein the active ingredient(s) is selected from a group consisting of tumulosic acid, dehydrotumolosic acid, dehydrotrametenolic acid, poricoic acid A, and combinations thereof. Particularly, the pulmonary injury is caused by particulate matter. The uses include a use of the active ingredient(s) in the manufacture of a composition used for regulating, preventing and/or treating pulmonary injury, and/or for regulating, preventing and/or treating pulmonary injury-related disease, a method comprising administering to a subject in need an effective amount of the active ingredient(s) so as to regulate, prevent and/or treat pulmonary injury, and/or to regulate, prevent and/or treat pulmonary injury-related disease, and providing a composition comprising the active ingredient(s). The active ingredients can be provided as a plant extract or a fungus extract. The composition is a food composition or a pharmaceutical composition.

The composition provided in accordance with the present invention can be a food composition or a pharmaceutical composition, wherein the food composition can be a health food, a dairy supplement, a functional food, a nutritional supplement food or a special nutritional food, and can be produced in products such as dairy products, meat products, breadstuff, pasta, cookies, troche, capsule, fruit juices, teas, sports beverages, nutrient beverages, etc., but is not limited to thereby.

Depending on the need, age, body weight, and health conditions of the subject, the health food, dairy supplement, functional food, nutritional supplement food or special nutritional food provided in accordance with the present invention can be taken at various frequencies, such as once a day, multiple times a day, or once every few days, etc. Depending on the needs of the particular population (e.g., elders, children, teenagers, pregnant woman, diabetes mellitus patients, renal disease patients, athletes, etc.), the amount of FU-LING extract, tumulosic acid, dehydrotumolosic acid, dehydrotrametenolic acid, and/or poricoic acid A in a health food, a dietary supplement, a functional food, a nutritional supplement food and a special nutritional food provided in accordance with the present invention can be also adjusted, for example, to the amount that should be taken daily.

The recommended daily dosage, use standards and use conditions for a specific population (e.g., elders, children, teenagers, pregnant woman, diabetes mellitus patients, renal disease patients, athletes, etc.), or the recommendations for a use in combination with another food product or medicament can be labeled on the outer package of health food, dietary supplement, functional food, nutritional supplement food and/or special nutritional food. Thus, users can take the health food, dietary supplement, functional food, nutritional supplement food and/or special nutritional food by him- or herself safely and securely without the instructions of a doctor, pharmacist or related executive.

Optionally, the food composition or pharmaceutical composition provided in accordance with the present invention can further comprise a suitable amount of additives, such as a flavoring agent, a toner, or a coloring agent for enhancing the palatability and the visual perception of the food composition or pharmaceutical composition, and/or a buffer, a conservative, a preservative, an antibacterial agent, or an antifungal agent for improving the stability and storability of the food composition or pharmaceutical composition.

Depending on the desired purpose, the pharmaceutical composition provided in accordance with the present invention can be present in any suitable form without special limitations. For example, the pharmaceutical compositions can be administered to a subject in need by an oral or parenteral (e.g., subcutaneous, intravenous, intramuscular, intraperitoneal, nasal, and skin) route. Depending on the form and purpose, suitable carriers can be chosen and used to provide the pharmaceutical composition, wherein the carriers include excipients, diluents, auxiliaries, stabilizers, absorbent retarders, disintegrating agents, hydrotropic agents, emulsifiers, antioxidants, adhesives, binders, tackifiers, dispersants, suspending agents, lubricants, hygroscopic agents, etc.

As a dosage form for oral administration, the pharmaceutical composition provided in accordance with the present invention can comprise any pharmaceutically acceptable carrier that will not adversely affect the desired effects of the active ingredients at least one of FU-LING extract, tumulosic acid, dehydrotumolosic acid, dehydrotrametenolic acid, and poricoic acid A), such as water, saline, dextrose, glycerol, ethanol or its analogs, cellulose, starch, sugar bentonite, or combinations thereof. The pharmaceutical composition can be provided in any suitable form for oral administration, such as in the form of a tablet (e.g., dragees), a pill, a capsule, granules, a pelvis, a fluidextract, a solution, a syrup, a suspension, a tincture, etc.

As for the form of injections or drips suitable for subcutaneous, intravenous, intramuscular, or intraperitoneal administration, the pharmaceutical composition provided in accordance with the present invention can comprise one or more ingredient(s), such as an isotonic solution, a salt-buffered saline (e.g., phosphate-buffered saline or citrate-buffered saline), a hydrotropic agent, an emulsifier, a 5% sugar solution, or other carriers to provide the pharmaceutical composition as an intravenous infusion, an emulsified intravenous infusion, a powder for injection, a suspension for injection, or a powder suspension for injection, etc. Alternatively, the pharmaceutical composition can be prepared as a pre-injection solid. The pre-injection solid can be provided in a form which is soluble in other solutions or suspensions, or in an emulsifiable form. A desired injection is provided by dissolving, the pre-injection solid in other solutions or suspensions or emulsifying it prior to being administered to a subject in need.

Depending on the need, age, body weight, and health conditions of the subject, the pharmaceutical composition provided in accordance with the present invention can be administered at various frequencies, such as once a day, multiple times a day, or once every few days, etc. The active ingredient(s) (i.e., at least one of FU-LING extract, tumulosic acid, dehydrotumolosic acid, dehydrotrametenolic acid, and poricoic acid A) in the pharmaceutical composition provided in accordance with the present invention can be adjusted depending on the requirements of practical application. In addition, the pharmaceutical composition can optionally comprise one or more other active ingredient(s), or to be used in combination with a medicament comprising one or more other active ingredient(s), to further enhance the effects of the pharmaceutical composition, or to increase the application flexibility and application adaptability of the preparation thus provided, as long as the other active ingredients do not adversely affect the desired effects of the active ingredients of the present invention.

The present invention also provides a method for regulating, preventing and/or treating pulmonary injury, and/or for regulating, preventing and/or treating pulmonary injury-related diseases, comprising administering to a subject in need an effective amount of the aforementioned active ingredients (i.e., at least one of FU-LING extract, tumulosic acid, dehydrotumolosic acid, dehydrotrametenolic acid, and poricoic acid A). The type, administered route, administered form, administered frequency, and uses in the related applications of the active ingredients are all in line with the above descriptions.

The present invention will be further illustrated in detail with specific examples as follows. However, the following examples are provided only for illustrating the present invention and the scope of the present invention is not limited thereby. The scope of the present invention will be indicated in the appended claims.

EXAMPLE

Preparation Examples

A. Preparation of FU-LING Extract

A-1. Herbal FU LING (habitat: Yunnan, China) was washed and its skin was peeled (hereinafter referred to as "FU-LING epidermis"), and the rest was meat (hereinafter referred to as "FU-LING meat").

A-2. Preparation of FU-LING Meat Extract (A-2-1) The FU-LING meat obtained from A-1 was soaked in 75% aqueous ethanol solution (FU-LING meat: 75% aqueous ethanol solution=1:8 in volume) at room temperature for 12 hours, and then decocted for 3 hours to provide a liquid extract. The foregoing extraction procedures were repeated three times. The liquid extracts obtained from the three extractions were combined and filtered to remove the insoluble and provide a crude extract. The ethanol contained in the crude extract was removed by vacuum concentration to provide a concentrated solution. The concentrated solution was dried by using a spray dryer to provide a FU-LING meat crude extract powder.

(A-2-2) The FU-LING meat crude extract powder obtained from A-2-1 was evenly dispersed in pure water at a volume ratio of crude extract powder:pure water=1:10 to provide a mixture. Sodium hydroxide was added into the mixture to provide a solution with an alkaline concentration of 1N (i.e., to increase the pH value of the mixture to about 12). Then, the solution was poured into a barrel that was maintained at a temperature of 70° C. with agitation until the reaction was completed. Thereafter, a concentrated hydrochloric acid (12N) was added into the barrel to neutralize the solution and decrease the pH value of the solution to 7, and then the liquid was removed by a centrifugation (1000 rpm) at room temperature (by a plate centrifuge) for 30 minutes and a filtration. The insoluble was collected. The insoluble was washed with pure water and then dried and ground into a powder. The powder thus obtained was then extracted by 95% ethanol at a volume ratio of insoluble matter: 95% ethanol=1:40. The foregoing extraction procedures were repeated three times. The extracts obtained from the three extractions were combined and concentrated by vacuum concentration to remove ethanol and provide a FU-LING meat extract (hereinafter refers to as "extract A").

(A-2-3) The extract A of FU-LING meat obtained from A-2-2 was evenly dispersed in pure water at a volume ratio of extract:pure water=1:20 to obtain a mixture. Sodium hydroxide was added into the mixture to increase the pH value of the mixture to be at least more than 11.7, and then the liquid was removed by a centrifugation (1000 rpm) at room temperature (by a plate centrifuge) for 30 minutes and a filtration. The insoluble was collected and dispersed in pure water to provide a solution. Thereafter, a 12N concentrated hydrochloric acid was added into the solution to decrease the pH value of the solution to 7, and then the liquid was removed by filtration. The remaining insoluble was washed with pure water and then as dried and ground into a FU-LING meat extract powder (hereinafter refers to as "extract B").

A-3, Preparation of FU-LING Epidermis Extract (A-3-1) The FU-LING epidermis obtained from A-1 was soaked in 75% aqueous ethanol solution (herbal FU-LING: 75% ethanol=1:8 in volume) at room temperature for 12 hours, and then decocted for 3 hours to provide a liquid extract. The foregoing extraction procedures were repeated three times. The liquid extracts obtained from the three extractions were combined and filtered to remove insoluble and provide a crude extract. The ethanol contained in the crude extract was removed by vacuum concentration to provide a concentrated crude extract. A suitable amount of water was added into the concentrated crude extract to remove water-soluble impurities. The insoluble sediment was collected and dried by using a spray dryer to provide a FU-LING epidermis crude extract powder.

(A-3-2) The FU-LING epidermis crude extract powder obtained from A-3-1 was mixed with 95% aqueous ethanol solution at a volume ratio of crude powder extract:ethanol solution=1:8 to provide a mixture. The mixture was subjected to an extraction for 3 hours to provide a liquid extract. The liquid extract was dried by using a spray dryer to provide a FU-LING epidermis extract (hereinafter refers to as "extract C").

A-4. Preparation of Mixed Herbal FU-LING Extract (A-4-1) The FU-LING epidermis and FU-LING meat obtained from A-1 (epidermis:meat=1:2) were soaked in 75% aqueous ethanol solution (mixed herbal FU-LING: 75% ethanol=1:8 in volume) at room temperature for 12 hours, and then decocted for 3 hours to provide a liquid extract. The foregoing extraction procedures were repeated three times. The liquid extracts obtained from the three extractions were combined and filtered to remove insoluble and provide a crude liquid extract. The ethanol contained in the crude extract was removed by vacuum concentration to provide a concentrated crude extract. A suitable amount of water was added into the concentrated crude liquid extract to remove water-soluble impurities. The insoluble sediment was concentrated by vacuum concentration to provide a mixed herbal FU-LING paste. The remaining mixed herbal FU-LING residue was also collected.

(A-4-2) The mixed herbal FU-LING paste obtained from A-4-1 was dried by using a spray dryer to provide a powder. The powder was mixed with 95% aqueous ethanol solution (powder:aqueous ethanol solution=1:8 in volume), and then decocted for 3 hours to provide a liquid extract. The liquid extract was dried by using a spray dryer to provide a mixed herbal FU-LING extract (hereinafter refers to as "extract D").

(A-4-3) The mixed herbal FU-LING residue provided by A-4-1 was mixed with pure water (mixed herbal FU-LUNG residue:pure water=1:10 in volume), and then decocted for 3 hours to provide a liquid extract. The foregoing extraction procedures were repeated twice. The liquid extracts obtained from the two extractions were combined and filtered to remove insoluble and provide a crude extract. Thereafter, the crude extract was mixed with the mixed herbal FU-LING paste obtained from A-4-4 to provide a mixture. The mixture was dried by using a spray dryer to provide a mixed herbal FU-LING extract (hereinafter refers to as "extract E").

A-5. Preparation of FU-LING Fermentation Product Extract (A-5-1) *Poria cocos* strains (deposited at Food industry Research and Development Institute (Taiwan) under the accession number BCRC 39126) was inoculated into malt extract agar (MEA) plate (mail extract: purchased from Micromed Scientific Products, Ltd., Taiwan, product no. 218630; agar: purchased from Micromed Scientific Products, Ltd., Taiwan, product no. LP0011) as a mycelial disk having a diameter of 5 mm, and then kept at a temperature of 27±5° C. and a relative humidity of 40±10% for about 6 days to be pre-activated. Alternatively, the pre-activation of *Poria cocos* strains can also be conducted by replacing the malt extract ager plate with potato dextrose agar (PDA) plate (purchased from Micromed Scientific Products, Ltd., product no. 254920).

(A-5-2) The MEA plate with the pre-activated *Poria cocos* strains (i.e., mycelial disks) growth thereon obtained from A-5-1 was used, and the mycelial diskson the plate surface were inoculated onto the substrate surface (the amount of the mycelial disks inoculated onto each substrate was that on ⅙ area of the plate surface). Thereafter, the inoculated substrates were placed at a temperature ranging from 20° C. to 35° C. and a relative humidity ranging from 30% to 70% in dark for weeks to mouths, and a FU-LING fermentation product was thus provided.

(A-5-3) The FU-LING fermentation product obtained from A-5-2 was dried and pulverized into powder by hot air drying at a temperature of 60° C. to provide a FU-LING fermentation product powder. The powder thus obtained was extracted with an alcohol extraction (95% aqueous ethanol solution was used) accompanied with an ultrasonic vortex to provide a liquid extract. The foregoing extraction procedures were repeated three times. The liquid extracts obtained from the three extractions were combined and filtered to remove insoluble to provide a crude extract. The ethanol contained in the crude extract was removed by vacuum concentration at a temperature of 60° C. to provide a FU-LING fermentation product extract (hereinafter refers to as "extract F").

B. Component Analysis of FU-LING Extract

The components of extract A to F obtained from [preparation example A] were determined by liquid chromatography coupled to diode array UV detection and mass spectrometry (LC/UV/MS) at a wavelength of 243 nm and 210 nm respectively.

The results show that extracts A to D and extract F all do not comprise *Poria cocos* polysaccharides. Extract A and extract B both comprise the components such as tumulosic acid, dehydrotumulosic acid, polyporenic acid C, and 3-epi-dehydrotumulosic acid. Extract C comprises the components such as pachymic acid, dehydropachymic acid, tumulosic acid, dehydrotumulosic acid, polyporenic acid C, 3-epi-dehydrotumulosic acid, dehydrotrametenolic acid, trametenolic acid, poricoic acid A, dehydroeburicoic acid, poricoic acid B, and eburicoic acid. Extracts D to F all comprise the components such as pachymic acid, dehydrotrametenolic acid, tumulosic acid, dehydrotumulosic acid, polyporenic acid C, 3-epi-dehydrotumulosic acid, dehydrotrametenolic acid, trametenolic acid, poricoic acid A, dehydroeburicoic acid, poricoic acid B, and eburicoic acid.

Thereafter, the content of each component contained in the extracts was quantified by high performance liquid chromatography (HPLC). The analysis results of extract A are shown in Table 1, the analysis results of extract B are shown in Table 2, and the analysis results of extract C are shown in Table 3.

TABLE 1

| Components | wt % |
| --- | --- |
| *Poria cocos* polysaccharides | — |
| pachymic acid (PA) | — |
| dehydropachymic acid (DPA) | — |
| tumulosic acid (TA) | 15.5 |
| dihydrotumulosic acid (DTA) | 6.59 |
| polyporenic acid C (PAC) | 2.44 |
| 3-epi-dehydrotumulosic acid (EDTA) | 4.13 |

TABLE 2

| Components | wt % |
| --- | --- |
| *Poria cocos* polysaccharides | — |
| pachymic acid (PA) | — |
| dehydropachymic acid (DPA) | — |
| tumulosic acid (TA) | 47.72 |
| dihydrotumulosic acid (DTA) | 18.42 |
| polyporenic acid C (PAC) | 2.93 |
| 3-epi-dehydrotumulosic acid (EDTA) | 0.81 |

TABLE 3

| Components | wt % |
| --- | --- |
| *Poria cocos* polysaccharides | — |
| pachymic acid (PA) | 2.70 |
| dehydropachymic acid (DPA) | 1.29 |
| tumulosic acid (TA) | 1.15 |
| dihydrotumulosic acid (DTA) | 2.56 |
| polyporenic acid C (PAC) | 2.74 |
| 3-epi-dehydrotumulosic acid (EDTA) | 0.36 |
| dehydrotrametenolic acid (DTTA) | 8.95 |
| trametenolic acid (TTA) | 4.87 |
| poricoic acid A (PAA) | 20.40 |
| dehydroeburicoic acid (DEA) | 9.05 |
| poricoic acid B (PAB) | 4.71 |
| eburicoic acid (EA) | 3.04 |

C. Preparation of the Active Ingredients in FU-LING Extract

C-1. The extract F provided by [Preparation example A] was dissolved evenly in methanol at a volume ratio of extract and methanol=1:500 to provide a mixture. Then, the mixture was filtered to remove the insoluble. The remaining filtrate was purified by preparative high performance liquid chromatography (a mixture of methanol and water was used as the mobile phase) at a wavelength of 243 nm and 210 nm respectively, and each portion of containing pachymic acid, dehydropachymic acid, tumulosic acid, dehydrotumulosic acid, polyporenic acid C, 3-epi-dehydrotumulosic acid, dehydrotrametenolic acid, trametenolic acid, poricoic acid A, dehydroeburicoic acid, poricoic acid B and/or eburicoic acid were collected. The collected portions were vacuum-concentrated to remove methanol and obtain pachymic acid, dehydropachymic acid, tumulosic acid, dehydrotumulosic acid, polyporenic acid C, 3-epi-dehydrotumulosic acid, dehydrotrametenolic acid, trametenolic acid, poricoic acid A, dehydroeburicoic acid, poricoic acid B and eburicoic acid respectively. The components contained in the extracts A to F provided by [preparation example A] can also be purified and isolated by the foregoing steps.

C-2, The pachymic acid, dehydropachymic acid, tumulosic acid, dehydrotumulosic acid, polyporenic acid C, 3-epi-dehydrotumulosic acid, dehydrotrametenolic acid, trametenolic acid, poricoic acid A, dehydroeburicoic acid, poricoic acid B, and eburicoic acid obtained from C-1 were detected by LC/UV/MS at a wavelength of 243 nm and 210 nm respectively, and the results show the purities of all component were all higher than 93%.

Example 1

Effect of FU-LING Extract and its Active Ingredients in Inhibiting the Expression and/or Activity of MMPs As indicated above, when an inflammatory response occurs in animal's pulmonary tissue, the active inflammatory cells will secret MMPs that will destroy the pulmonary tissue structure, cause more serious pulmonary injury, and lead to the decrement in or the loss of pulmonary functions. To investigate whether the FU-LING extract and its active ingredients are effective in inhibiting the secretion, expression and activity of MMPs of inflammatory cells or not, gelatin zymography and Western blot were conducted to determine the inhibitory rate of FU-LING extract and its active ingredients on the LPS-activated active expression of MMP-9 (i.e., a sum of the secretion level, expression level and activity of MMP-9) of a rat alveolar macrophage cell line, NR8383 cells.

(1-1)

Rat alveolar macrophage NR8383 cells (purchased from ATCC, CRL-2192™) were divided into fifteen groups and separately cultivated with the following media for 24 hours:

(1) Blank group: a macrophage growth medium;
(2) Control group: a macrophage growth medium containing 1 μg/mL LPS (purchased from Sigma-Aldrich);
(3) Positive control group: a macrophage growth medium containing 1 μg/mL LPS and 1 μM dexamethasone (a type of corticosteroid; abbreviated as "Dex"; purchased from Sigma-Aldrich);
(4) Extract A group (including three sub-groups): a macrophage growth medium containing 1 μg/mL LPS and the extract A provided by [preparation example A-2-2], wherein the extract A is present in the three sub-groups at a concentration of 6.25, 12.5 and 25 μg/mL respectively;
(5) Extract B group (including three sub-groups): a macrophage growth medium containing 1 μg/mL LPS and the extract B provided by [preparation example A-2-3], wherein the extract B is present in the three sub-groups at a concentration of 6.25, 12.5 and 25 µg/mL respectively;

(6) TA group (including three sub-groups): a macrophage growth medium containing 1 µg/mL LPS and the tumulosic acid (TA) provided by [preparation example C-1], wherein the tumulosic acid (TA) is present in the three sub-groups at a concentration of 3.13, 6.25 and 12.5 µg/mL respectively; and (7) DTA group (including three sub-groups): a macrophage growth medium containing 1 µg/mL LPS and the dehydrotumulosic acid (DTA) provided by [preparation example C-1], wherein the dehydrotumulosic acid (DTA) is present in the three sub-groups at a concentration of 3.13, 6.25 and 12.5 µg/mL, respectively.

Thereafter, the medium of each group was collected and respectively subjected to the following procedures. A 10% polyacrylamide gel containing 0.2% gelatin was used to carry out the sodium dodecyl sulfate polyacrylamide gel electrophoresis (SDS-PAGE). After the electrophoresis was completed, the gel was sequentially soaked in 2.5% Triton X-100 solution for 90 minutes to remove SDS, soaked in distillation-distillation water (ddH$_2$O) for 30 minutes, and placed in a reaction solution (50 mM Tris-HCl buffer containing 10 mM CaCl$_2$ and 0.02% NaN$_3$) at a temperature of 37° C. for 18 hours. After the foregoing reaction was completed, the gel was stained by a Coomassie blue staining solution, and the image of stained gel was taken and subjected to an image analysis. The image intensity (the image intensity was calculated based on the size of area and the shade of color) of highlight band (i.e., the gelatin in this area was degraded by MMPs, wherein the area locating around 95 kD molecular weight) on the gel of each group can reflect the active expression of MMP-9 of rat alveolar macrophage NR8383 cells under different conditions (the relative active expression of MMP-9 was calculated by serving the results of the blank group as 0% and serving that of the control group as 100%). The results are shown in Table 4.

TABLE 4

| Group | | Relative active expression of MMP-9 (%) |
|---|---|---|
| Blank group | | 0 |
| Control group (concentration of LPS: 1 µg/mL) | | 100 |
| Positive control (concentration of LPS: 1 µg/mL; concentration of Dex: 1 µM) | | 100 |
| Extract A group | 6.25 µg/mL | 100 |
| | 12.5 µg/mL | 59.5 |
| | 25 µg/mL | 45.5 |
| Extract B group | 6.25 µg/mL | 72.4 |
| | 12.5 µg/mL | 35.3 |
| | 25 µg/mL | 0 |
| TA group | 3.13 µg/mL | 60.6 |
| | 6.25 µg/mL | 28.4 |
| | 12.5 µg/mL | 0 |
| DTA group | 3.13 µg/mL | 79.7 |
| | 6.25 µg/mL | 83.9 |
| | 12.5 µg/mL | 80.7 |

The experimental results show that the rat alveolar macrophage NR8383 cells treated with 1 µg/mL ITS exhibited a significantly increased active expression of MMP-9.

As shown in Table 4, when the concentration of LPS is 1 µg/mL, Dex cannot inhibit the active expression of MMP 9, However, extract A, extract B and tumulosic acid (i.e., the primary component of extract A and extract B) are all effective in inhibiting the LPS-induced increment in the active expression of MMP-9, and a significant dose-response relationship was observed in the effects of extract B and tumulosic acid. 25 µg/mL of extract B and 12.5 µg/mL of tumulosic acid both can completely inhibit the LPS induced increment in the active expression of MMP-9. These results indicate that extract A, extract B and tumulosic acid (i.e., the primary component of extract A and extract B) are all effective in decreasing the increment in the active expression of MMPs, and their effects are better than that of Dex, and thus, can be used for developing a food composition or a pharmaceutical composition for assisting in regulation of active expression of MMPs in animals.

(1-2)

Rat alveolar macrophage NR8383 cells were divided into twenty-eight groups and separately cultivated with the following media for 24 hours:

(1) Blank group: a macrophage growth medium;

(2) Control group: a macrophage growth medium containing 1 µg/mL LPS;

(3) Positive control group: a macrophage growth medium containing 1 µg/mL LPS and 5 µM Prednisolone (a type of corticosteroid; abbreviated as "Pred"; purchased from Sigma-Aldrich);

(4) Extract C (including five sub-groups): a macrophage growth medium containing 1 µg/mL LPS and the extract C provided by [preparation example A-3-2], wherein the extract C is present in the five sub-groups at a concentration of 0.78, 1.56, 6.25 and 12.5 µg/mL respectively;

(5) Extract D (including five sub-groups): a macrophage growth medium containing 1 µg/mL UPS and the extract D provided by [preparation example A-4-2], wherein the extract D is present in the five sub-groups at a concentration of 0.78, 1.56, 3.13, 6.25 and 12.5 respectively;

(6) Extract E (including five sub-groups): a macrophage growth medium containing 1 µg/mL LPS and the extract E provided from [preparation example A-4-3], wherein the extract E is present in the five sub-groups at a concentration of 0.78, 1.56, 3.13, 625, and 12.5 respectively;

(7) DATA group (including five sub-groups): a macrophage growth medium containing 1 µg/mL LPS and the dehydrotrametenolic acid (DTTA) provided by [preparation example C-1], wherein the dehydrotrametenolic acid (DTTA) is present in the five sub-groups at a concentration of 0.39, 0.78, 1.56, 3.13 and 6.25 µg/mL respectively; and (8) PAA group (including live sub-groups): a macrophage growth medium containing 1 µg/mL LPS and the poricoic acid A (PAA) provided from [preparation example C-1], wherein the poricoic acid A (PAA) is present in the five sub-groups at a concentration of 6.25, 12.5, 25, 50 and 100 respectively.

Thereafter, the medium of each group was collected and analyzed by the analyzing procedures same as that of (1-1). The results are shown in Table 5.

TABLE 5

| Group | Relative active expression of MMP-9 (%) |
|---|---|
| Blank group | 0 |
| Control group (concentration of LPS: 1 µg/mL) | 100 |

TABLE 5-continued

| Group | | Relative active expression of MMP-9 (%) |
|---|---|---|
| Positive control group (concentration of LPS: 1 µg/mL; concentration of Pred: 5 µM) | | 97 |
| Extract E group | 0.78 µg/mL | 65 |
| | 1.56 µg/mL | 58 |
| | 3.13 µg/mL | 47 |
| | 6.25 µg/mL | 65 |
| | 12.5 µg/mL | 65 |
| DTTA group | 0.39 µg/mL | 91 |
| | 0.78 µg/mL | 99 |
| | 1.56 µg/mL | 79 |
| | 3.13 µg/mL | 72 |
| | 6.25 µg/mL | 74 |
| PAA group | 6.25 µg/mL | 82 |
| | 12.5 µg/mL | 77 |
| | 25 µg/mL | 60 |
| | 50 µg/mL | 35 |
| | 100 µg/mL | 18 |

The experimental results show the rat alveolar macrophage NR8383 cells treated with 1 µg/mL LPS exhibited a significantly increased active expression of MMP-9, However, Pred (served as a positive control in this experiment) cannot inhibit the 1 µg/mL LPS-induced active expression of MMP-9. Extract C and extract D did not have a significant effect on inhibiting the 1 µg/mL LPS-induced increment in active expression of MMP-9.

As shown in table 5, when the concentration of LPS was 1 µg/mL, Pred cannot effectively inhibit the active expression of MMP-9. However, extract E, dehydrotrametenolic acid and poricoic acid A are all effective in inhibiting the LPS-induced increment in active expression of MMP-9, and a much better effect presenting in a significant dose-response relationship was observed in poricoic acid A. These results indicate that extract E, dehydrotrametenolic acid and poricoic acid A are all effective in decreasing the increment in active expression of MMPs, and their effects are better than that of Pred (it is predictable that their effects are also better than that of Dex), and thus, can be used for developing a food composition or a pharmaceutical composition for assisting in regulation of active expression of MMPs in animals.

(1-3)

Rat alveolar macrophage NR8383 cells were divided into six groups and separately cultivated with the following media for 24 hours:

(1) Control group: a macrophage growth medium containing 0.01 µg/mL LPS;

(2) Positive control group: a macrophage growth medium containing 0.01 µg/mL LPS and 1 µM Dex; and (3) Extract A group (including four sub-groups): a macrophage growth medium containing 0.01 µg/mL LPS and the extract A provided by [preparation example A-2-2], wherein the extract A is present in the four sub-groups at a concentration of 6.25, 12.5, 25 and 50 µg/mL respectively.

Thereafter, the proteins in the cells of each group were extracted and then subjected to a Western blot to measure the expression level of pro-form MMP-9 (i.e., the zymogen form of MMP-9), active-form MMP-9 and MMP-12. The relative expression level of pro-form MMP-9, active-form MMP-9 and MMP-12 of each group was calculated by using the results of the control group as a basis (i.e., the expression level of control group was served as 1-fold). The results are shown in FIG. 1A to FIG. 1C.

Figure 1A:
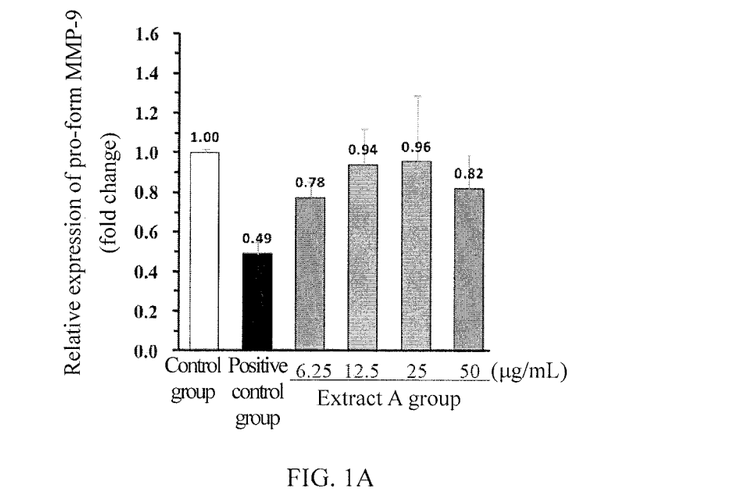
FIG. 1A shows the relative expression level of pro-form MMP-9.
Figure 1B:
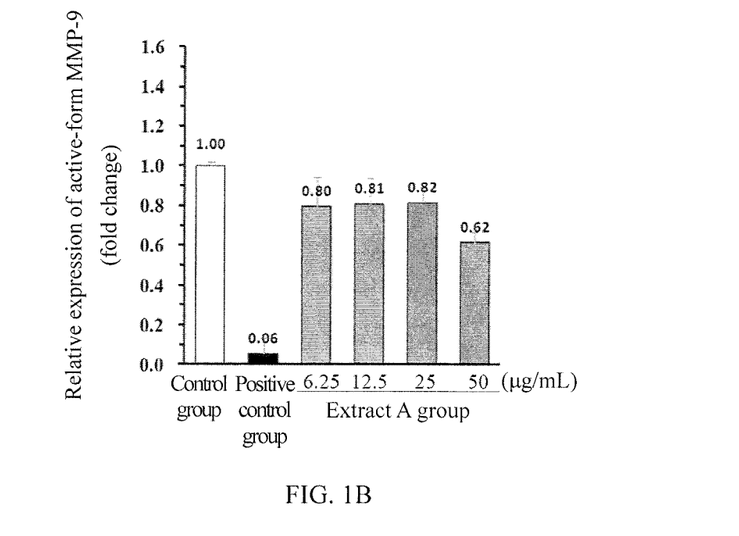
FIG. 1B shows the relative expression level of active-form MMP-9.
Figure 1C:
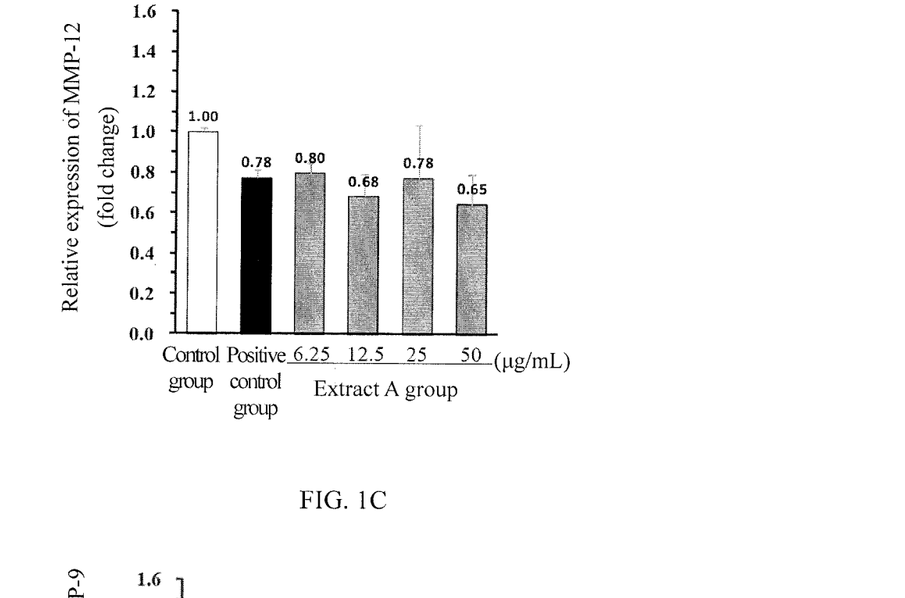
FIG. 1C shows the relative expression level of MMP-12.

As shown in FIG. 1A to FIG. 1C, in comparison with the control group, the expression levels of pro-form MMP-9, active-form MMP-9 and MMP-12 in the cells of extract A group were lower, and the 50 µg/mL extract A exhibited an inhibitory rate of 38% and 35% respectively on the expression levels of active-form MMP-9 and MMP-12.

(1-4)

Rat alveolar macrophage NR8383 cells were divided into ten groups and separately cultivated with the following media for 24 hours:

(1) Control group: a macrophage growth medium containing 0.01 µg/mL LPS;

(2) Positive control group: a macrophage growth medium containing 0.01 µg/mL LPS and 1 µM Dex;

(3) TA group (including four sub-groups): a macrophage growth medium containing 0.01 µg/mL LPS and the tumulosic acid (TA) provided by [preparation example C-1], wherein the tumulosic acid (TA) is present in the four subgroups at a concentration of 1.56, 3.13, 6.25 and 12.5 µg/mL respectively; and (4) PAA group (including four sub-groups): a macrophage growth medium containing 0.01 µg/mL LPS and the poricoic acid A (PAA) provided by [preparation example C-1], wherein the poricoic acid A (PAA) is present in the four sub-groups at a concentration of 6.25, 12.5, 25 and 50 µg/mL respectively.

Thereafter, the proteins in the cells of each group were extracted and then subjected to a Western blot to measure the expression level of pro-form MMP-9 (i.e., the zymogen form of MMP-9), active-form MMP-9 and MMP-12. The relative expression levels of pro-form MMP-9, active-form MMP-9 and MMP-12 of each group was calculated by using the results of the control group as a basis (i.e., the expression level of control group was served as 1-fold). The results are shown in FIG. 2A to FIG. 2C, and FIG. 3A to FIG. 3C.

Figure 2A:
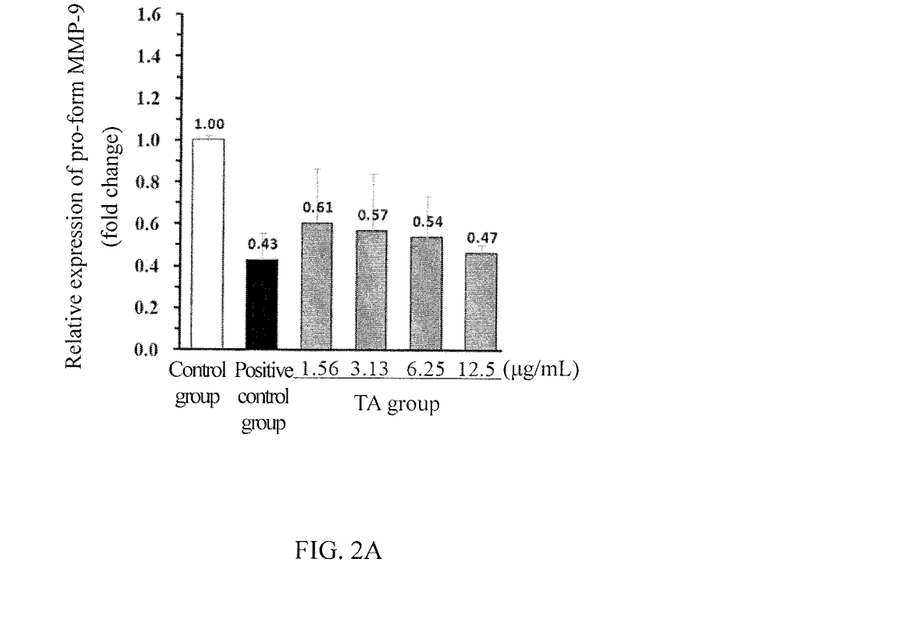
FIG. 2A shows the relative expression level of pro-form MMP-9.
Figure 2B:
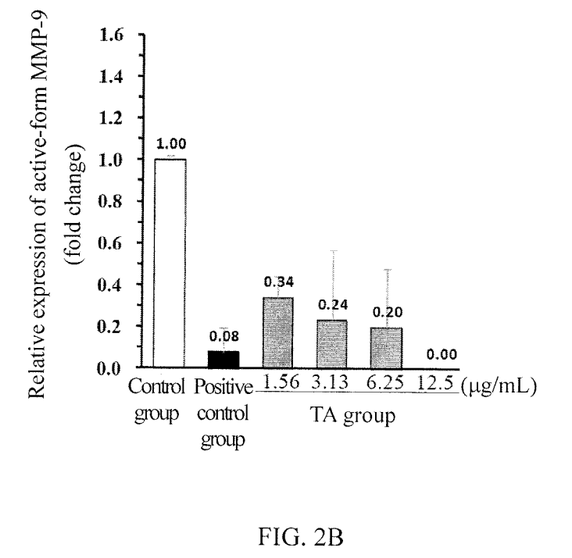
FIG. 2B shows the relative expression level of active-form MMP-9.
Figure 2C:
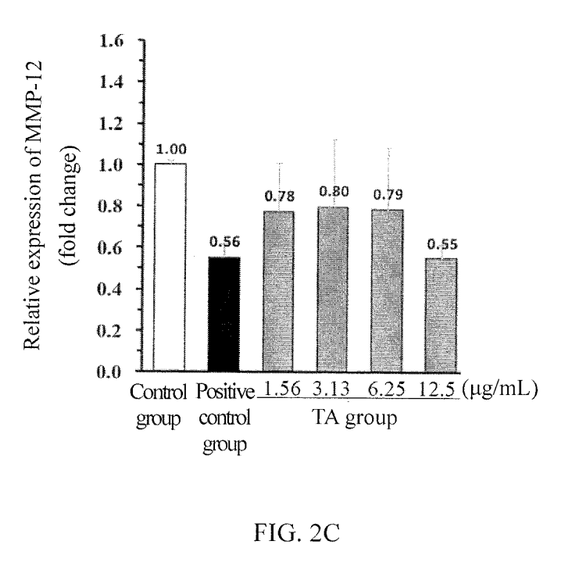
FIG. 2C shows the relative expression level of MMP-12.
Figure 3A:
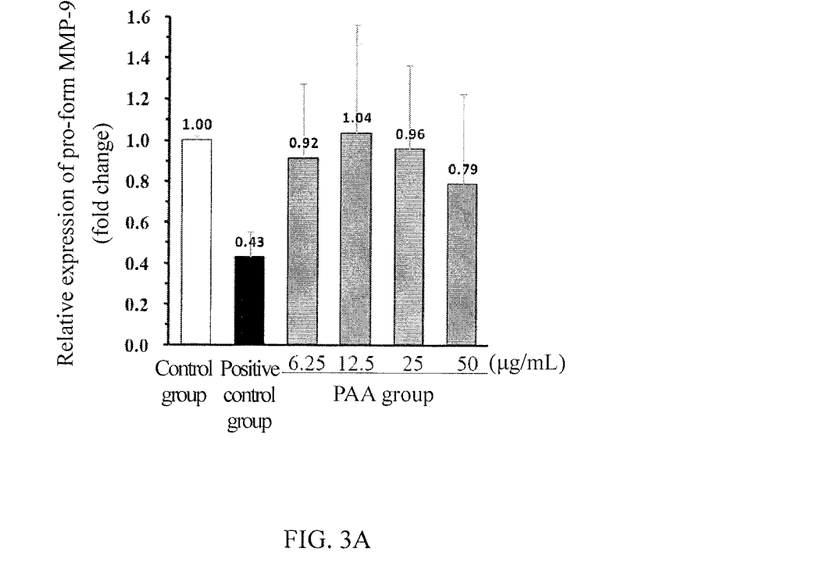
FIG. 3A shows the relative expression level of pro-form MMP-9.
Figure 3B:
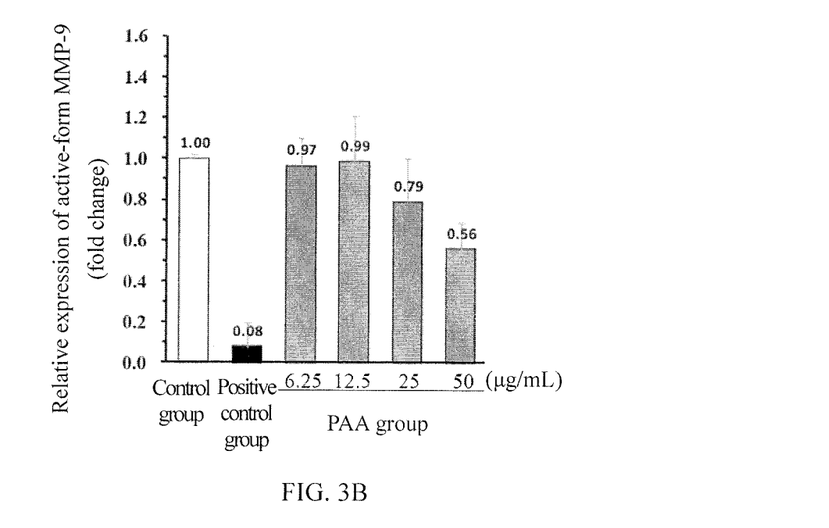
FIG. 3B shows the relative expression level of active-form MMP-9.
Figure 3C:
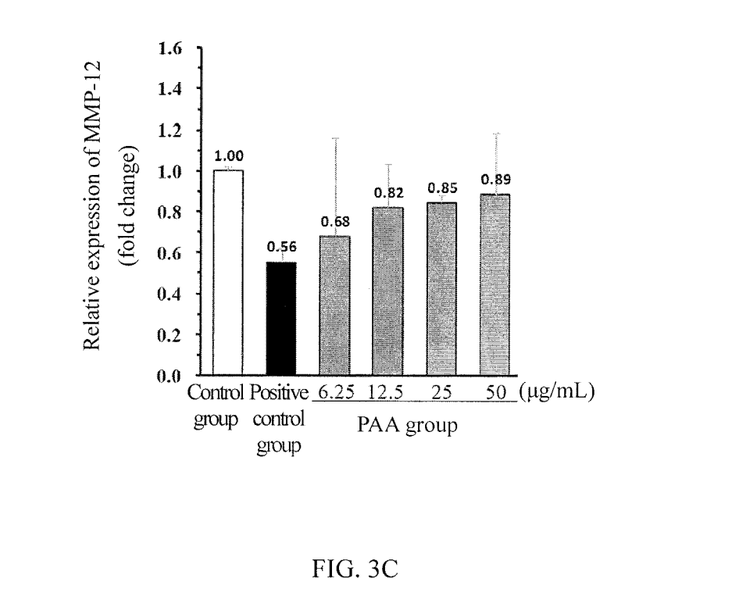
FIG. 3C shows the relative expression level of MMP-12.

As shown in FIG. 2A to FIG. 2C, in comparison with the control group, the expression levels of pro-form MMP-9, active-form MMP-9 and MMP-12 in the cells of TA group were lower, and the 12.5 µg/mL tumulosic acid exhibited an inhibitory rate of 53%, 100% and 45% respectively on the expression levels of pro-form MMP-9, active-form MMP-9 and MMP-12. As shown in FIG. 3A to FIG. 3C, poricoic acid A is effective in inhibiting the expression levels of pro-form MMP-9, active-form MMP-9 and MMP-12, and shows the most significant inhibitory effect on active-form MMP-9. The inhibitory rate of poricoic acid A on active-form MMP-9 can be up to 44%.

The results of (1-3) and (1-4) show again that extract A, tumulosic acid and poricoic acid A are all effective in inhibiting the increment in active expression of MMPs, and thus, can be used for developing a food composition or a pharmaceutical composition for assisting in regulation of active expression of MMPs in animals.

Example 2

Effects of FU-LING Extracts and its Active Ingredients in Inhibiting the Secretion/Accumulation of Collagen As indicated above, the hyperactive expression of MMPs will cause pulmonary injury. Under the most circumstances, the response mechanisms in animals will activate, for example, macrophages will secret TGF-β and TGF-β which can promote the lung fibroblasts to secret collagen, so that the damaged tissues can be recovered. However, the hypersecretion of collagen will also lead to lung fibrosis. To investigate whether FU-LING extracts and its active ingredients are effective in regulating, protecting and/or treating the pulmonary injury-related diseases such as lung fibrosis or not, the Picrosirius red (PSR) staining was conducted as a semi-quantification of collagen, so that the inhibitory rate of FU-LING extract and its active ingredients on the TGFβ-induced intracellular accumulation of collagen in myofibroblast WI38 cells can be determined.

(2-1)

Myofibroblast WI38 cells (purchased from ATCC, product no. CCL75™) were divided into ten groups and separately cultivated with the following media for 48 hours:
 (1) Blank group: a myofibroblast growth medium;
 (2) Control group: a myofibroblast growth medium containing 1 ng/mL TGF-β (purchased from R&D system);
 (3) Positive control group: a myofibroblast growth medium containing 1 ng/mL TGF-β and 200 μg/mL Pirfenidone (abbreviated as "Pir"; purchased from Sigma-Aldrich);
 (4) Extract A (including four sub-groups): a myofibroblast growth medium containing 1 ng/mL TGF-β and the extract A provided by [Preparation example A-2-2], wherein the extract A is present in the four sub-groups at a concentration of 12.5, 25, 50 and 100 μg/mL respectively; and
 (5) Extract B (including three sub-groups): a myofibroblast growth medium containing 1 ng/ml, TGF-β and the extract B provided by [Preparation example A-2-3], wherein the extract B is present in the four sub-groups at a concentration of 12.5, 25 and 50 μg/mL respectively.

Thereafter, the media were replaced by methanol to fix the cells at a temperature of −20° C. for 1 to 2 hours. After that, the cells were washed with PBS, and then stained with 0.1% PSR staining agent (purchased from Sigma-Aldrich) at room temperature for 4 hours. The stained cells were washed with 0.1% acetic acid, and then lysed with 0.1N sodium hydroxide to provide a lysate. The OD540 (i.e., the absorbance at a wavelength of 540 nm) of the lysate was measured. OD540 value of each group represents the content of collagen in each group, reflecting the content of collagen in fibroblast WI38 cells under different circumstances (the relative content of collagen in each group was calculated by serving the result of blank group as 0% and serving the result of control group as 100%). The results show in Table 6.

TABLE 6

| Group | | Relative content of collagen (%) |
|---|---|---|
| Blank group | | 0 |
| Control group | | 100 |
| Positive control group | | 69 |
| Extract A group | 12.5 μg/mL | 90 |
| | 25 μg/mL | 85 |
| | 50 μg/mL | 63.5 |
| | 100 μg/mL | 0 |
| Extract B group | 12.5 μg/mL | 97 |
| | 25 μg/mL | 60.5 |
| | 50 μg/mL | 0 |

As shown in Table 6, extract A or extract B both are effective in inhibiting the TGFβ-induced secretion/accumulation or intracellular collagen, and a high concentration of extract A or extract B exhibited an effect better than that of Pir (served as a positive control in this experiment). On the other hand, the median effective doses (abbreviated as "ED50"; i.e., the concentration of extract A or extract B which can inhibit the increasing level of TGFβ-induced collagen accumulation to 50% of that of control group) of extract A and extract B were respectively calculated by linear regression, and the ED50 of extract A is 50 μg/mL to 80 μg/mL and the ED50 of extract B is 26 μg/mL to 28 μg/mL. These results indicate that extract A and extract B are both effective in inhibiting the collagen hypersecretion and hyperaccumulation of pulmonary cells, and thus, can be used for regulating, preventing and/or treating the pulmonary injury-related diseases (especially for lung fibrosis), and extract B exhibits an effect slightly better than that of extract A.

(2-2)

Myofibroblast WI38 cells were divided into twenty-eight groups and separately cultivated with the following media for 24 hours:
 (1) Blank group: a myofibroblast growth medium;
 (2) Control group: a myofibroblast growth medium containing 1 ng/mL TGF-β (purchased from R&D system);
 (3) Positive control group: a myofibroblast growth medium containing 1 ng/mL TGF-β and 200 μg/mL Pirfenidone (abbreviated as "Pir"; purchased from Sigma-Aldrich);
 (4) Extract C group (including five sub-groups): a myofibroblast growth medium containing 1 ng/mL TGF-β and the extract C provided by [preparation example A-3-2], wherein the extract C is present in the five sub-groups at a concentration of 0.78, 1.56, 3.1.25, 6.25 and 12.5 μg/mL respectively;
 (5) Extract D group (including five sub-groups): a myofibroblast growth medium containing 1 ng/mL TGF-β and the extract D provided by [preparation example A-4-2], wherein the extract D is present in the five sub-groups at a concentration of 0.78, 1.56, 3.13, 6.25 and 12.5 μg/mL respectively;
 (6) Extract E group (including five sub-groups): a myofibroblast growth medium containing 1 ng/mL TGF-β and the extract E provided by [preparation example A-4-3], wherein the extract E is present in the five sub-groups at a concentration of 0.78, 1.56, 3.13, 6.25 and 12.5 μg/mL respectively;
 (7) DTTA group (including five sub-groups): a myofibroblast growth medium containing 1 ng/mL TGF-β and the dehydrotrametenolic acid (DTTA) provided by [preparation example C-1], wherein the dehydrotrametenolic acid (DTTA) is present in the five subgroups at a concentration of 0.39, 0.78, 1.56, 3.13 and 6.25 μg/mL respectively; and
 (8) PAA group (including five sub-groups): a myofibroblast growth medium containing 1 ng/mL TGF-β and the poricoic acid A (PAA) provided by [preparation example C-1], wherein the poricoic acid A (PAA) is present in the five sub-groups at a concentration of 6.25, 12.5, 25, 50 and 100 μg/mL respectively.

Thereafter, the medium of each group was collected and analyzed by the analyzing procedures same as that of (2-1). The results show in Table 7.

TABLE 7

| Group | | Relative content of collagen (%) |
|---|---|---|
| Blank group | | 0 |
| Control group | | 100 |
| Positive control group | | 0 |
| Extract C group | 0.78 μg/mL | 18 |
| | 1.56 μg/mL | 15 |
| | 3.13 μg/mL | 70 |
| | 6.25 μg/mL | 20 |
| | 12.5 μg/mL | 0 |
| Extract D group | 0.78 μg/mL | 70 |
| | 1.56 μg/mL | 100 |
| | 3.13 μg/mL | 40 |

TABLE 7-continued

| Group | | Relative content of collagen (%) |
|---|---|---|
| | 6.25 µg/mL | 49 |
| | 12.5 µg/mL | 56 |
| Extract E group | 0.78 µg/mL | 100 |
| | 1.56 µg/mL | 65 |
| | 3.13 µg/mL | 49 |
| | 6.25 µg/mL | 15 |
| | 12.5 µg/mL | 21 |
| DTTA group | 0.39 µg/mL | 25 |
| | 0.78 µg/mL | 100 |
| | 1.56 µg/mL | 25 |
| | 3.13 µg/mL | 53 |
| | 6.25 µg/mL | 70 |
| PAA group | 6.25 µg/mL | 82 |
| | 12.5 µg/mL | 78 |
| | 25 µg/mL | 48 |
| | 50 µg/mL | 0 |
| | 100 µg/mL | 0 |

As shown in Table 7, extract C, extract D, extract E and their primary ingredients (dehydrotrametenolic acid and poricoic acid A) are all effective in inhibiting the TGFβ-induced accumulation of intracellular collagen, and extract E and poricoic acid A both exhibits an effect presenting in a dose-response relationship. These results show extract C, D, F, and primary ingredients thereof (dehydrotrametenolic acid and poricoic acid A) are all effective in inhibiting the collagen hypersecretion and hyperaccumulation in pulmonary cells, and thus, can be used for regulating, preventing and/or treating the pulmonary injury-related diseases (especially for lung fibrosis).

Example 3

Effects of the Active Ingredients of FU-LING Extract in Inhibiting the Expression of Mucins As indicated above, the hypersecretion of mucus in airway can be observed in the patients suffering from pulmonary injury-related diseases, such as chronic obstructive pulmonary disease and emphysema, and the mucus hypersecretion is associated with the overexpression of mucins in pulmonary tissue. Symptoms like the increased sputum production will occur in the patients suffering from the mucin hypersecretion in airway, and the increased sputum will accumulate in the airway and lung, thereby making the airway narrow and increasing respiratory resistance. To investigate the effects of active ingredients of FU-LING extract in regulating, preventing, and/or treating the pulmonary injury-related diseases, such as chronic obstructive pulmonary disease and emphysema, a Western blot was conducted to measure the inhibitory rate of active ingredients of FU-LING extract (tumulosic acid and poricoic acid A) on the LPS-induced expression of Mucin 5AC in human lung epithelial NCI-H929 cells.

Human lung epithelial NCI-H929 cells were divided into ten groups and separately cultivated with the following media for 24 hours:

(1) Control group: an epithelial cell growth medium containing 1 µL LPS;

(2) Positive control group: an epithelial cell growth medium containing 1 µg/mL LPS and 10 µM Dex;

(3) TA group (including four sub-groups): an epithelial cell growth medium containing 1 µg/mL and the tumulosic acid (TA) provided by [preparation example C-1], wherein the tumulosic acid (TA) is present in the four sub-groups at a concentration of 1.56, 3.13, 6.25 and 12.5 µg/mL respectively; and (4) PAA group (including four sub-groups): an epithelial cell growth medium containing 1 µg/mL LPS the poricoic acid A (PAA) provided by [preparation example C-1], wherein the poricoic acid A (PAA) is present in the four sub-groups at a concentration of 6.25, 12.5, 25 and 50 µg/mL respectively.

Thereafter, the proteins in the cells of each group were extracted and then subjected to a Western blot to measure the expression level of Mucin 5AC. The relative expression level of Mucin 5AC of each group was calculated by using the results of the control group as a basis (i.e., the expression level of control group was served as 1-fold). The results are shown in FIG. 4A and FIG. 4B.

Figure 4A:
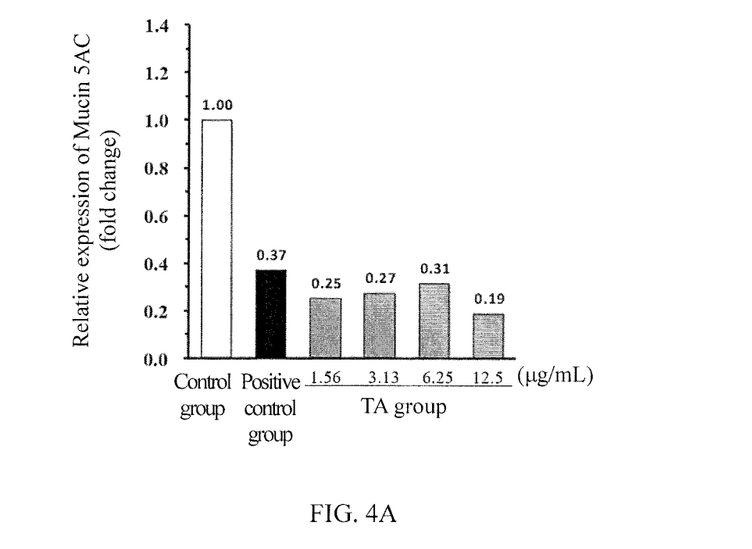
FIG. 4A shows the results of control group, positive control group, and tumulosic acid group.
Figure 4B:
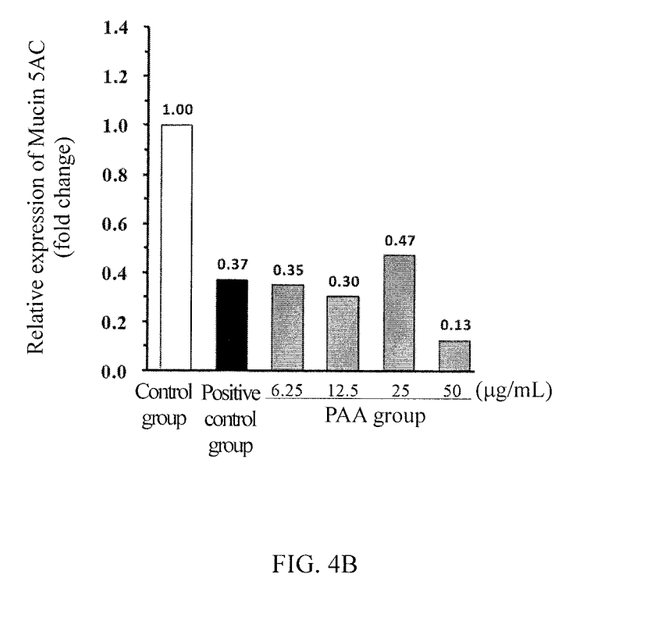
FIG. 4B shows the results of control group, positive control group, and poricoic acid A group.

As shown in FIG. 4A and FIG. 4B, in comparison with the control group, both TA and PAA are effective in inhibiting the LPS-induced expression of Mucin 5AC, wherein, a low-dose (1.56 µg/mL) and a high-dose (12.5 µg/mL) of tumulosic acid exhibited an inhibitory rate up to 75% and 81% respectively, and a low-dose (6.25 µg/mL) and a high-dose (50 µg/mL) of poricoic acid A exhibited an inhibitory rate up to 63% and 87% respectively.

These results indicate that, the active ingredients of FU-LING extract such as tumulosic acid and poricoic acid A, are effective in inhibiting the LPS-induced increased expression of Mucin 5AC, and thus, can be used for developing a food composition or a pharmaceutical composition for assisting in regulation of expression of Mucin 5AC in animals, thereby alleviating the overproduction of sputum.

As shown in the above examples, FU-LING extract and its active ingredients in accordance with the present invention are effective in inhibiting the LPS-induced increment in the active expression of MMPs and/or expression of mucins, and/or inhibiting the TGFβ-induced collagen hypersecretion and hyperaccumulation, and thus, can be used for regulating, preventing, and/or treating pulmonary injury, especially the pulmonary injury caused by particulate matter.

What is claimed is:

1. A method for regulating and/or treating pulmonary injury, and/or for regulating and/or treating a pulmonary injury-related disease, consisting of administering to a subject in need thereof a composition consisting of (i) an effective amount of a FU-LING (*Poria cocos*) extract and (ii) a toner, a buffer, a preservative, and/or a pharmaceutically acceptable carrier, wherein the pulmonary injury is induced by matrix metalloproteinase-12 (MMP-12) disorder, wherein the pulmonary injury-related disease is at least one of chronic obstructive pulmonary disease (COPD), idiopathic pulmonary fibrosis (IPF), chronic bronchitis (CB), acute respiratory distress syndrome (ARDS), bronchopulmonary dysplasia (BPD), bronchiolitis obliterans (BO), and cryptogenic organizing pneumonia (COP), and wherein the FU-LING extract is a C1-C4 alcohol extract of FU-LING.

2. The method as claimed in claim 1, wherein the FU-LING extract comprises at least one of tumulosic acid (TA), dehydrotumulosic acid (DTA), dehydrotrametenolic acid (DTTA) and poricoic acid A (PAA).

3. The method as claimed in claim 1, wherein the FU-LING extract is at least one of an extract of FU-LING meat, an extract of FU-LING epidermis, and an extract of FU-LING fermentation product, wherein the FU-LING fermentation product is obtained by inoculating the *Poria cocos* (Schw.) Wolf onto a substrate and then fermenting in dark for several weeks to several months.

4. The method as claimed in claim 1, wherein the FU-LING extract is free of FU-LING polysaccharides.

5. The method as claimed in claim 1, wherein the FU-LING extract is administered to the subject in an amount that is sufficient to decrease the expression and/or activity of MMP-12, thereby regulating and/or treating pulmonary injury, and/or regulating and/or treating pulmonary injury-related diseases.

6. The method as claimed in claim 1, wherein the FU-LING extract is administered to the subject in an amount that is sufficient to decrease the expression of mucins, thereby regulating and/or treating pulmonary injury, and/or regulating and/or treating pulmonary injury-related diseases.

7. The method as claimed in claim 6, wherein the mucin is mucin 5AC.

8. The method as claimed in claim 1, wherein the FU-LING extract is administered to the subject in an amount that is sufficient to increase lung capacity, reduce respiratory resistance, reduce coughing, and/or reduce sputum production.

9. The method as claimed in claim 1, wherein the FU-LING extract is administered to the subject in an amount that is sufficient to regulate and/or treat pulmonary injury induced by particulate matter (PM).

10. A method for regulating and/or treating pulmonary injury, and/or for regulating and/or treating a pulmonary injury-related disease, consisting of administering to a subject in need thereof a composition consisting of (i) an effective amount of an active ingredient and (ii) a toner, a buffer, a preservative, and/or a pharmaceutically acceptable carrier, wherein the active ingredient is tumulosic acid, dehydrotumulosic acid, dehydrotrametenolic acid, or poricoic acid A, wherein the pulmonary injury is induced by MMP-12 disorder, and wherein the pulmonary injury-related disease is at least one of chronic obstructive pulmonary disease, idiopathic pulmonary fibrosis, chronic bronchitis, acute respiratory distress syndrome, bronchopulmonary dysplasia, bronchiolitis obliterans, and cryptogenic organizing pneumonia.

11. The method as claimed in claim 10, wherein the active ingredient is administered as a fungal extract.

12. The method as claimed in claim 10, wherein the active ingredient is administered to the subject in an amount that is sufficient to decrease the expression and/or activity of MMP-12, thereby regulating and/or treating pulmonary injury, and/or regulating and/or treating pulmonary injury-related diseases.

13. The method as claimed in claim 10, wherein the active ingredient is administered to the subject in an amount that is sufficient to decrease the expression of mucins, thereby regulating and/or treating pulmonary injury, and/or regulating and/or treating pulmonary injury-related diseases.

14. The method as claimed in claim 13, wherein the mucin is mucin 5AC.

15. The method as claimed in claim 10, wherein the active ingredient is administered to the subject in an amount that is sufficient to increase lung capacity, reduce respiratory resistance, reduce coughing, and/or reduce sputum production.

16. The method as claimed in claim 10, wherein the active ingredient is administered to the subject in an amount that is sufficient to regulate and/or treat the pulmonary injury induced by particulate matter (PM).

* * * * *